(12) United States Patent
Pierce et al.

(10) Patent No.: US 9,757,096 B2
(45) Date of Patent: Sep. 12, 2017

(54) BIOLOGICAL SAMPLE COLLECTION DEVICE

(71) Applicant: GE HEALTHCARE UK LIMITED, Little Chalfont (GB)

(72) Inventors: Alan Stuart Pierce, Cardiff (GB); Simon Laurence John Stubbs, Cardiff (GB); David Gwyn Treharne, Cardiff (GB); Cheryl Louise Potts, Cardiff (GB)

(73) Assignee: GE Healthcare UK Limited, Little Chalfont (GB)

( * ) Notice: Subject to any disclaimer, the term of this patent is extended or adjusted under 35 U.S.C. 154(b) by 219 days.

(21) Appl. No.: 14/354,933

(22) PCT Filed: Oct. 31, 2012

(86) PCT No.: PCT/EP2012/071602
§ 371 (c)(1),
(2) Date: Apr. 29, 2014

(87) PCT Pub. No.: WO2013/064558
PCT Pub. Date: May 10, 2013

(65) Prior Publication Data
US 2014/0303518 A1  Oct. 9, 2014

(30) Foreign Application Priority Data
Oct. 31, 2011 (GB) .................................. 1118753.1

(51) Int. Cl.
*A61B 10/00* (2006.01)
*B01L 3/00* (2006.01)

(52) U.S. Cl.
CPC ...... *A61B 10/0051* (2013.01); *A61B 10/0096* (2013.01); *B01L 3/5055* (2013.01);
(Continued)

(58) Field of Classification Search
CPC ............ A61B 10/0045; A61B 10/0051; A61B 10/0096; A61B 2010/0208;
(Continued)

(56) References Cited

U.S. PATENT DOCUMENTS

| 4,540,366 A | * | 9/1985 | Belzile ................. A61F 15/001 |
| | | | 401/130 |
| 5,308,580 A | * | 5/1994 | Clark ..................... B01L 3/502 |
| | | | 422/419 |

(Continued)

FOREIGN PATENT DOCUMENTS

| WO | WO 98/48280 | 10/1998 |
| WO | WO 2007/099344 | 9/2007 |
| WO | WO 2008/099196 | 8/2008 |

*Primary Examiner* — Sean Dougherty
(74) *Attorney, Agent, or Firm* — Eversheds Sutherland (US) LLP

(57) ABSTRACT

Biological samples, such as saliva, are commonly collected on a swab and subsequently transferred to an absorbent storage medium. Embodiments of the present invention provide a biological sample collection device 600 comprising a collection portion 620 and a body portion 610, the body portion including a holding portion 652 for holding a biological sample storage medium (618 FIG. 1), and a sample collection/transfer means. The collection portion 620 can be arranged in a first position shown in FIG. 4, separated from the body portion for collecting a sample. The device employs depressible latches (630, 640 FIG. 6) to control the movements of the collection portion.

16 Claims, 4 Drawing Sheets

(52) U.S. Cl.
CPC ........... *B01L 3/5023* (2013.01); *B01L 3/5029* (2013.01); *B01L 2300/021* (2013.01); *B01L 2300/022* (2013.01); *B01L 2300/043* (2013.01); *B01L 2300/0816* (2013.01); *B01L 2300/0825* (2013.01)

(58) Field of Classification Search
CPC ....... A61B 10/0266; B01L 3/50; B01L 3/502; B01L 3/5023; B01L 3/5029; B01L 3/5055; B01L 2300/043; A01K 11/001–11/003
See application file for complete search history.

(56) References Cited

U.S. PATENT DOCUMENTS

| | | | |
|---|---|---|---|
| 5,980,828 A * | 11/1999 | McClintock | B01L 3/5023 |
| | | | 422/417 |
| 2004/0161855 A1* | 8/2004 | Kvasnik | B01L 3/545 |
| | | | 436/165 |
| 2006/0246598 A1 | 11/2006 | Dai et al. | |
| 2008/0196517 A1 | 8/2008 | Harvey et al. | |
| 2010/0106057 A1* | 4/2010 | Harvey | B01L 3/5023 |
| | | | 600/573 |
| 2010/0185116 A1* | 7/2010 | Al-Mohizea | A61B 10/0233 |
| | | | 600/564 |
| 2013/0211287 A1* | 8/2013 | Decaluwe | A01K 11/003 |
| | | | 600/562 |

* cited by examiner

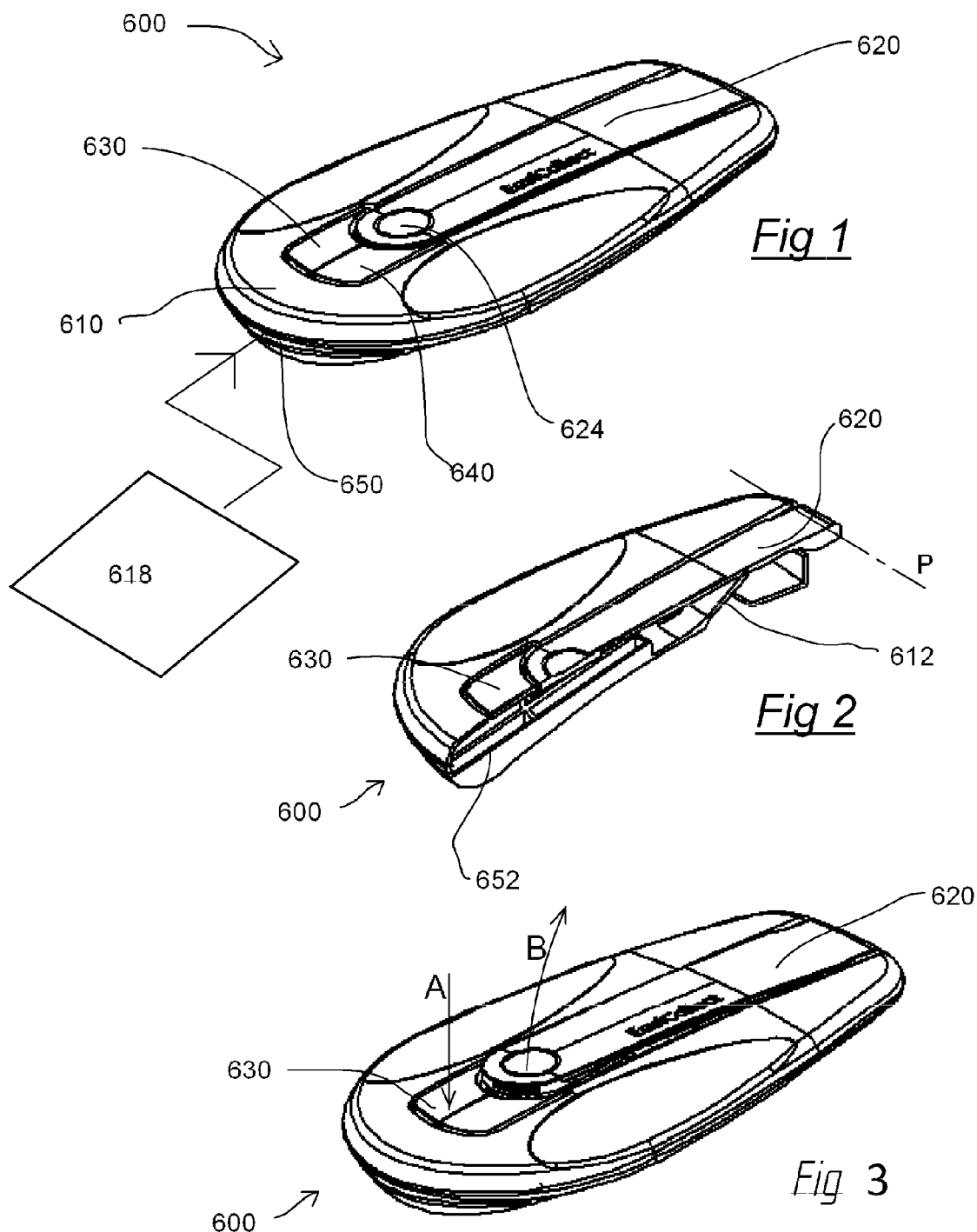

BIOLOGICAL SAMPLE COLLECTION DEVICE

CROSS-REFERENCE TO RELATED APPLICATIONS

This application is a filing under 35 U.S.C. 371 of international application number PCT/EP2012/071602, filed Oct. 31, 2012, published on May 10, 2013 as WO 2013/064558, which claims priority to application number 1118753.1 filed in Great Britain on Oct. 31, 2011.

FIELD OF THE INVENTION

The present invention relates to a device for collecting and storing biological samples.

BACKGROUND OF THE INVENTION

Biological samples, such as saliva taken for DNA profiling in criminal investigations, are commonly taken by swabbing a liquid containing biological material with an absorbent collection medium. Such collection media are, by necessity, exposed, and are therefore vulnerable to contamination. To maintain the integrity of the samples, they are typically transferred to and held in an absorbent storage medium, which may comprise a membrane impregnated with chemicals for stabilising the sample. The samples are allowed to dry and, once dry, the biological storage medium can be stored or transported to a testing facility for analysis.

Such methods of transferring biological samples from the collection medium to the storage medium typically involve bringing the collection medium into physical contact with the storage medium, perhaps with the application of a moderate amount of mechanical force; some of the liquid sample is then drawn by capillary action into the sample storage medium. Conventionally, this is a manual process and therefore consistent and uniform transfer of the biological sample from the collection medium to the storage medium depends heavily on the skill of the operator.

US2008/196517 proposes an integrated collection, transfer, and storage device into which a biological sample storage medium may be inserted. The device comprises a sample collection surface that can be brought into physical contact with the sample storage medium. It has been noted that the device illustrated in US2008/196517 is not simple to use and requires two hands to operate. Consequently, operation of the device is sometimes difficult in the field. Also, the construction of the device is such that direct contact between the operator and the collection portion of the device is necessary to transfer biological material; this is undesirable, as it may result in contamination of the sample and/or discomfort for the operator. Further, the force applied by an operator to cause transfer of the biological material may be uneven, causing the resulting transfer to be inconsistent and non-uniform.

Embodiments of the present invention address the problems mentioned above.

SUMMARY OF THE INVENTION

In accordance with a first aspect of the present invention, there is provided a biological sample collection device, comprising:

a body portion having an area for accepting a biological sample storage medium; and a sample collection portion including a biological sample collection medium, said sample collection portion being connected to said body portion for relative movement said relative movement allowing the positioning of the collection portion relative to the body portion at least into: an open position whereby the collection portion extends away from the body portion to allow collection of the sample on said collection medium; a transfer position whereby the collection medium and the storage medium can be brought into contact to allow at least partial transfer of the sample collected on said collection medium onto said storage medium; and into a closed position intermediate the first and second positions; the device including a releasable latch for holding the sample collection portion in both said transfer and closed positions, and for selectively releasing the collection portion to allow the movement from the closed to the open position, or to allow the movement from the transfer position to the closed position; the device being characterised in that the latch is formed from at least two depressible controls each separately operable for allowing said movement from the closed to the open position, and for allowing said movement from the transfer to the closed position.

In an embodiment, the device further includes a further depressible control for causing the collection portion to move from the open position to the transfer position.

Preferably, the at least two depressible controls each comprise a cantilevered button, moveable away from the collection portion to allow movement of the collection portion.

In an embodiment, the body portion includes a recess for accepting the sample collection portion, the recess being open to the area for accepting the sample storage medium, and wherein, when accepted into the area, the sample storage medium is substantially inaccessible from the recess when the collection portion is in the transfer or closed positions.

In an embodiment, when the transfer and closed positions are obtained, the collection portion is substantially within the recess.

In an embodiment, when the third position is obtained the collection portion has a surface which lies within the recess, substantially flush with an outer surface of the body portion.

Preferably, the outer surface and the collection portion, when in the closed position defines a substantially continuously curved external surface.

In an embodiment, the relative movement is rotational movement substantially about a pivot axis extending through the body portion.

In an embodiment the collection portion is urged toward the open position by means of a resilient part connected to or forming part of the body portion.

Preferably, said urging is resisted by a stop at or adjacent the open position.

Further features and advantages of the invention will become apparent from the following description of illustrative embodiments of the invention, given by way of example only, which is made with reference to the accompanying drawings.

BRIEF DESCRIPTION OF THE DRAWINGS

FIGS. 1, 3, 4, and 5 show perspective views of a biological sample collection device a according to the present invention;

FIG. 2 shows a sectional view of the device shown in FIG. 1;

DETAILED DESCRIPTION OF THE INVENTION

Figure 4:
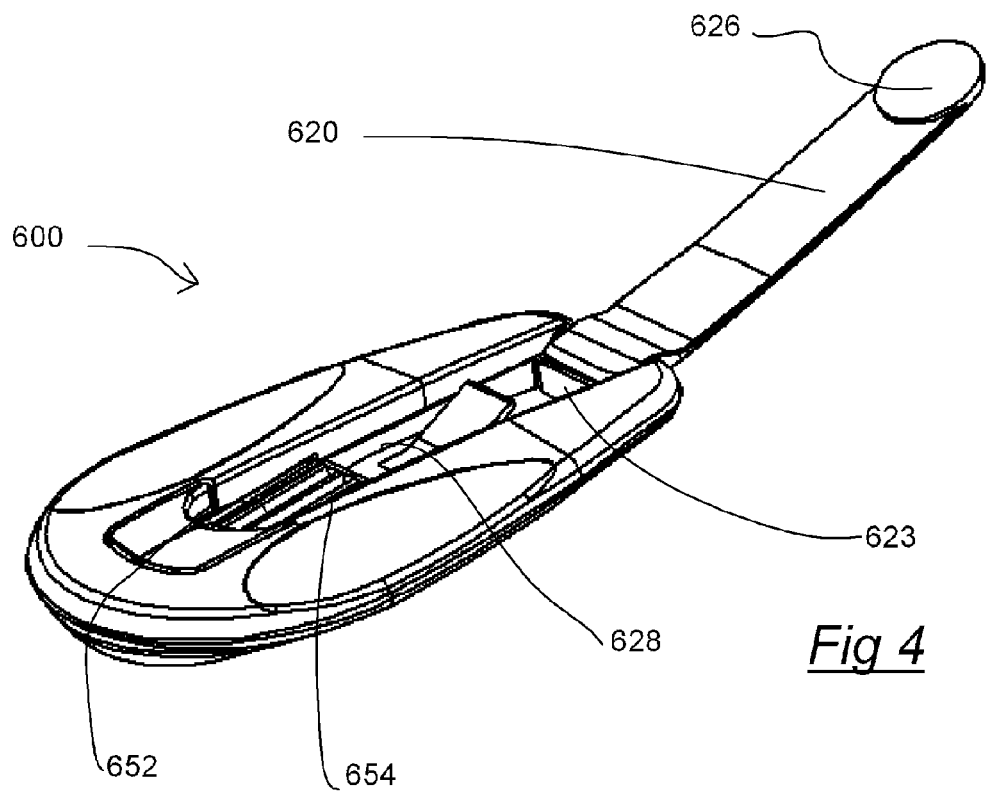

Referring to FIG. 1 there is shown a biological sample collection device 600. This device has a body portion 610 and a relatively moveable collection arm portion 620 shown in a closed position held adjacent the body 610. In addition the device has three depressible controls in this case in the form of latch buttons 624, 630 and 640, described in more detail below. A biological sample storage medium 618 usually supplied in a card form as described above, can be inserted into a slot 650 which accepts the medium into the body 610.

FIG. 2 shows a vertical mid-section through the device 600. The arm 620 is pivotable about a pivot axis P, and is urged to move by a resilient tab 612. However, the arm 620 is restrained from such movement by the latch button 630. In this figure, there is shown an internal area 652 which houses the storage medium 618 in use once inserted.

FIG. 3 shows latch button 630 in a depressed position, pushed by a user in the direction of arrow A, such that the arm 620 is then free to pivot upwardly in the direction of arrow B.

FIG. 4 shows the arm 620 in its fully extended collection or open position, prevented from further pivoting by a stop member 623. The now extended arm 620 includes a foam pad medium 626 which, as explained above, is used for biological sample collection. The extended arm 620 reveals a recess 628 in which the arm sits when not extended. It is apparent from FIG. 6 that the recess allows the arm to sit flush in the body 610, meaning that the body will then have a generally continuously curved outer surface with no substantial discontinuities or protuberances. Such a shape fits comfortably in a user's hand or pocket, for carrying, for example to a crime scene. The recess 628 is open to the area or portion 652 which accommodates the sample storage medium 618. The area 652 is bounded top and bottom by ribs 654 which improve drying of the sample storage medium following transfer of a biological sample from the pad 626 to the medium.

Figure 5:
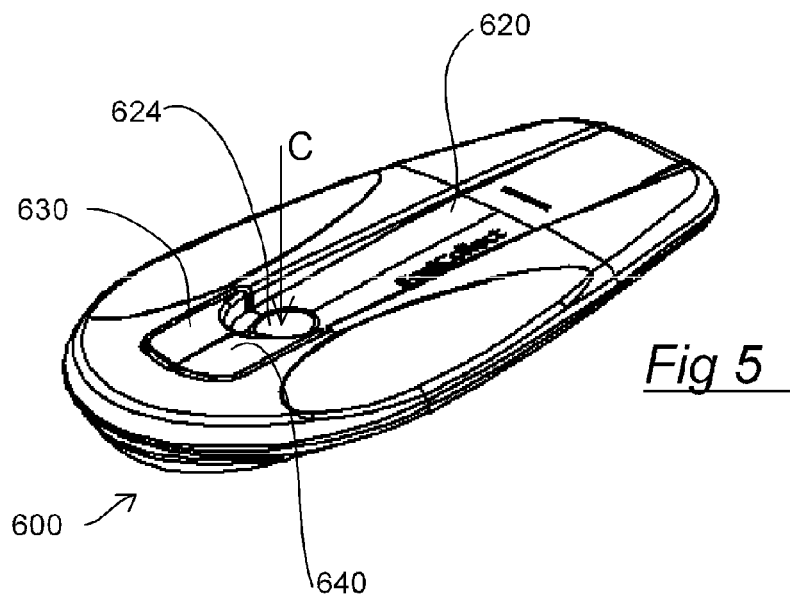

FIG. 5 shows the arm 620 in a transfer position, where the button 624 has been pushed in the direction of arrow C. This action forces the arm below the latch buttons 630 and 640 and causes transfer of the sample from the pad 626 to the storage medium 618 in the storage area 652. In practice this position is held for about 10 seconds, whereafter, the button 640 is depressed to allow the arm 620 to be urged again into the closed position which is the same position shown in FIG. 1.

In the closed position, the storage medium can dry, and either the whole device 600, or the removed sample storage medium 618 can be shipped for DNA/RNA analysis. It will be noted that the storage medium is not accessible when the arm 620 is closed. This prevents accidental contamination of the storage medium.

Figure 6:
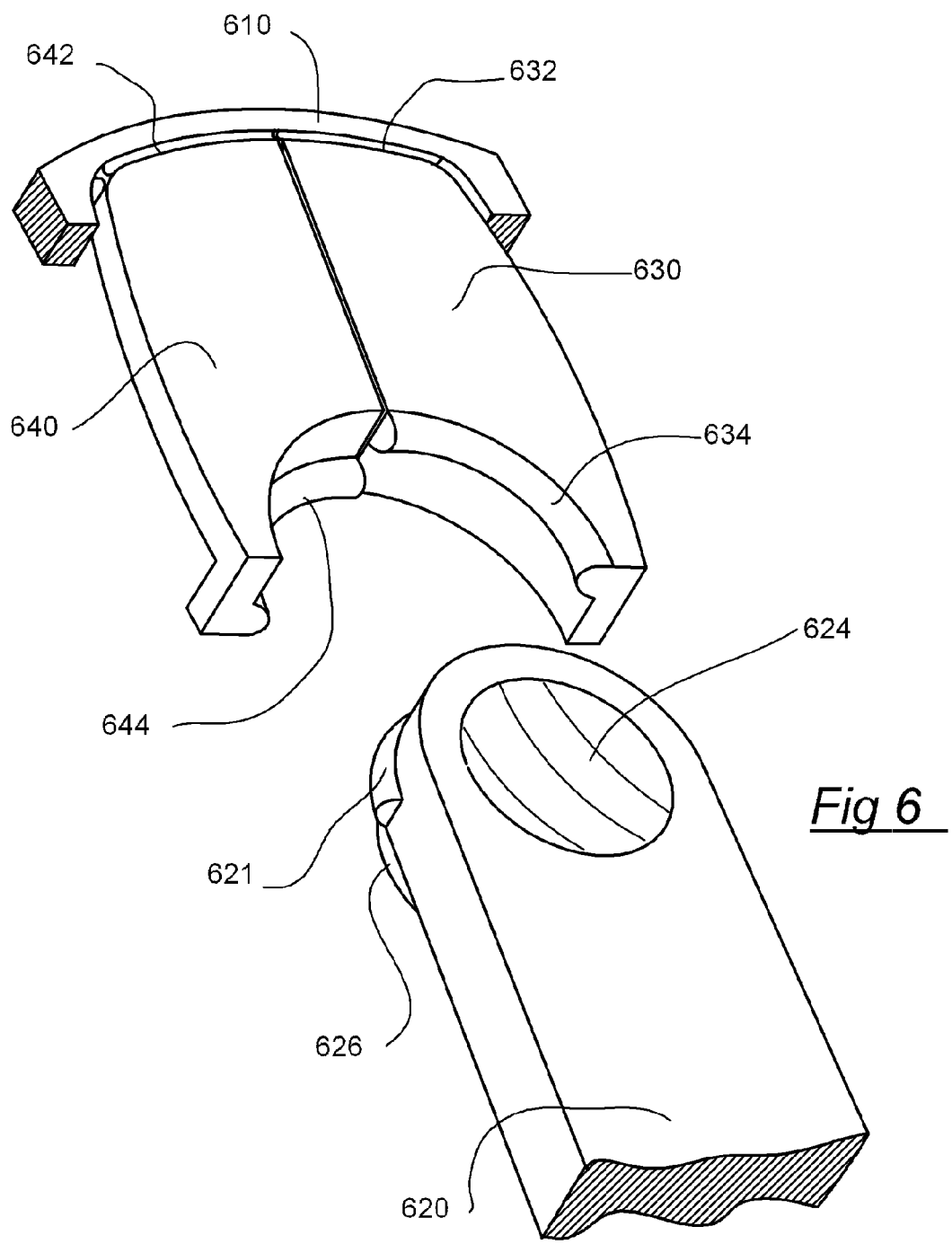
FIG. 6 shows an enlarged perspective view of components of the device shown in FIG. 1.

FIG. 6 shows the latch mechanism in enlarged and exploded detail. The latch buttons 630 and 640 pivot generally via a so called 'living hinge' which in this case is respective flexible plastics necked portions 632 and 642 of the body 610. Each latch button 630 and 640 is resiliently cantilevered about the hinges 632 and 642, and each has a detent 634 and 644 respectively, at their distal ends, which, when the buttons 620 and 640 are in their undisturbed positions shown, will interfere with the movement of an opposing detent 621 on the end of the arm 620. When depressed, the respective detents of the buttons will move out of interference with the opposing detent 62. Shown also is the further latch button 624 formed on the back of the arm 620.

FIGS. 7a to 7e illustrate the operating cycle of the device.

Figure 7A:
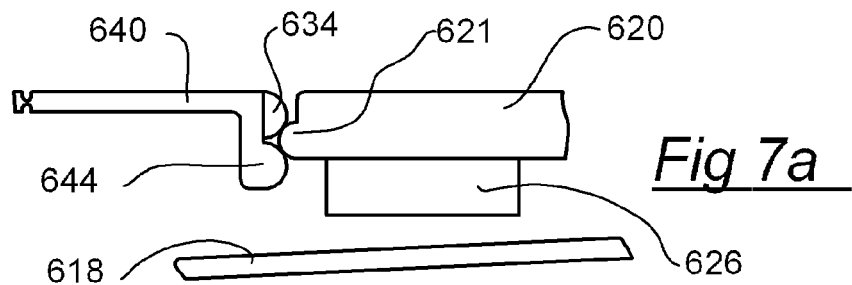
FIGS. 7a to 7e show, schematically, the operation of components illustrated in FIG. 6.

FIG. 7a shows the position of the buttons 630 and 640 with respect to the arm 620, corresponding to FIG. 1. In this position the opposing detent 621 is captured between detent 634 and detent 644 so that the arm 620 is prevented from moving upwardly and downwardly, so the arm remains in the closed position.

Figure 7B:
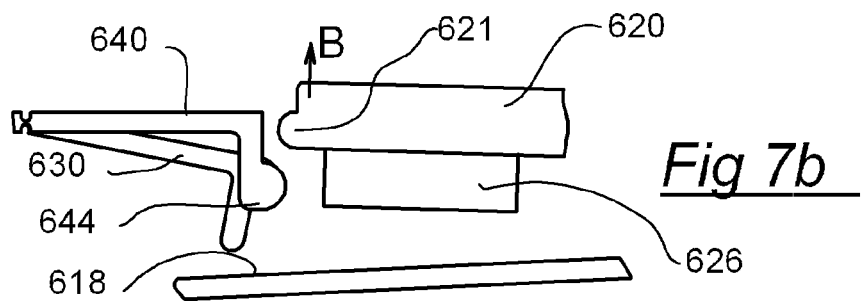

FIG. 7b shows the button 630 depressed, which in turn releases the arm 620 for upward movement in the direction of arrow B as shown in FIG. 2. The arm is then extended into the open, collection, position as shown in FIG. 3 and a biological sample is then collected.

Figure 7C:
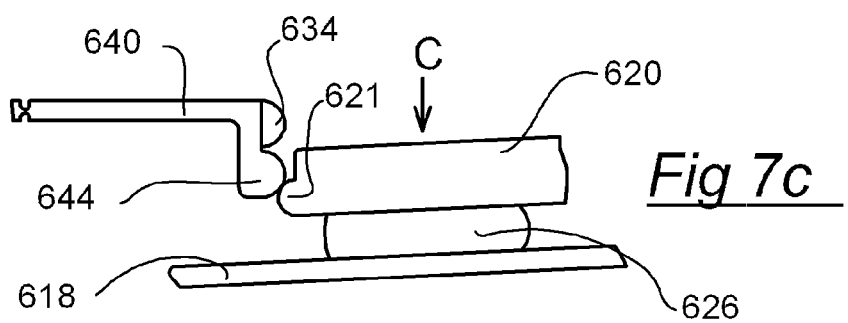

FIG. 7c shows the arm 620 now in the transfer, position, corresponding to FIG. 4. The opposing detent 621 has been forced over the detents 634 and 644, by pressing button 624 in the direction of arrow C, so that it is captured on the underside of the detent 644. In this position the pad 626 maintains contact with the sample storage medium 618. It will be noted that the storage medium 618 is aligned with the pad 626 to give substantially even contact force between the pad 626 and the medium 618.

Figure 7D:
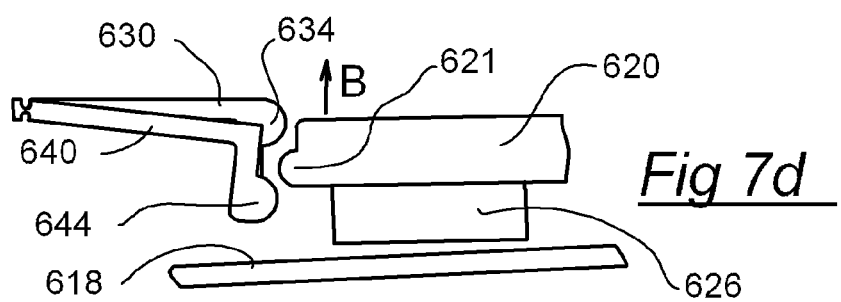
Figure 7E:
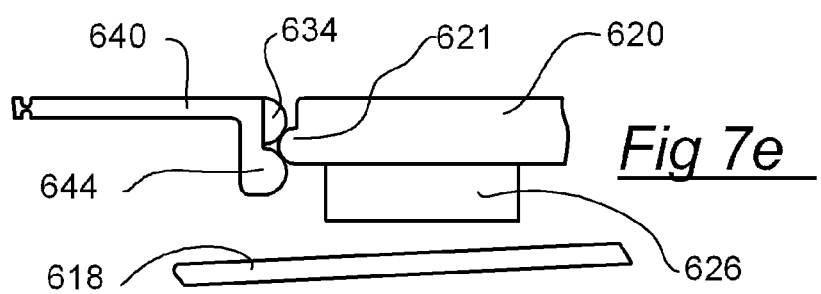

FIG. 7d shows the button 640 depressed so as to release the opposing detent 621 and allow the arm 620 to rise to the point shown in FIG. 7e, where again the further detent 621 is captured between the two detents 634 and 644 when the button 640 is released. In this closed position, the device can be shipped, or the medium 618 can be removed and shipped separately.

The detents shown are merely one example of many mechanical controls which could be employed to afford the positions of the arm as described above. For example, in place of protruding detents, recesses or grooves could be used on the arm 620 or on the buttons 630 or 640 cooperating with complementary features on the opposing parts.

More generally, the biological sample collection device 600 described above are supplied with a storage medium, for example the card 618 in place. However, in some circumstances the storage medium may be supplied separately from the respective device. Typically, the device is for single-use; however, in some applications the collection and storage mediums described may be replaceable.

The biological sample device 600 described above may comprise an identification tag comprising identification information. The tag may be printed directly onto the device, or be incorporated onto an adhesive label, or be added to the device by any other means. The tag may comprise textual and/or graphical information including sample identification numbers, donor details, and/or a barcode relating to such details stored remotely in a database. Other types of tag may be used, for example an RFID tag.

The device 600 may be manufactured from a plastics material using an injection moulding process. The plastics material should be compliant enough to allow temporary deformation of resilient parts of the device that are required to deform, when subjected to a suitable externally applied force, and to return to their original positions, upon removal of the externally applied force. The plastics material may also be selected such that it does not easily build up a static charge when handled, since such static charge can cause problems such as different collection devices sticking together, interfering with handling. An exemplary suitable plastics material is polypropylene homopolymer resin. However, any other suitable plastics material could be used as an alternative.

The above described biological sample collection devices are typically used for collection of biological samples such as saliva, blood or other bodily fluids. Samples collected by operation of the devices may be subjected to processing such as DNA or RNA amplification procedures, for example as polymerase chain reaction (PCR) procedures.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A biological sample collection device, comprising:
   a body portion having an area for accepting a biological sample storage medium; and
   a sample collection portion including a biological sample collection medium, said sample collection portion being connected to said body portion for relative movement, said relative movement allowing the positioning of the sample collection portion relative to the body portion at least into:
      an open position whereby the sample collection portion extends away from the body portion to allow collection of a biological sample on said biological sample collection medium;
      a transfer position whereby the sample collection portion is positioned such that the biological sample collection medium and the biological sample storage medium can be brought into contact to allow at least partial transfer of the sample collected on said biological sample collection medium onto said biological sample storage medium; and
      a closed position whereby the sample collection portion is positioned intermediate its location in the open position and the transfer position;
   the device including a releasable latch for holding the sample collection portion in both said transfer and closed positions, and for selectively releasing the sample collection portion to allow movement from the closed position to the open position, and to allow movement from the transfer position to the closed position,
   the device being characterised in that the latch is formed from at least two depressible controls each separately operable for allowing said movement from the closed to the open position, and for allowing said movement from the transfer to the closed position, and
   the device including a resilient part connected to or forming part of the body portion, wherein the resilient part is arranged to push against the sample collection portion and urge the sample collection portion toward the open position when the sample collection portion is in the closed position.

2. The biological sample collection device of claim 1, wherein the device further includes a further depressible control for causing the sample collection portion to move from the open position to the transfer position.

3. The biological sample collection device of claim 1 wherein the at least two depressible controls each comprise a cantilevered latch, interfering with movement of the sample collection portion, but moveable out of interference therewith to allow movement of the sample collection portion.

4. The biological sample collection device of claim 1, wherein the body portion includes a recess for accepting the sample collection portion, the recess being open to the area for accepting the biological sample storage medium, and wherein, when accepted into the area, the biological sample storage medium is substantially inaccessible from the recess when the sample collection portion is in the transfer or closed positions.

5. The biological sample collection device of claim 4, wherein when the transfer and closed positions are obtained, the sample collection portion is substantially within the recess.

6. The biological sample collection device of claim 4, wherein when the closed position is obtained, the sample collection portion has a surface which lies within the recess, substantially flush with an outer surface of the body portion.

7. The biological sample collection device of claim 6, wherein the outer surface and the sample collection portion, when in the closed position, form part of a continuously curved external surface of the body portion.

8. The biological sample collection device of claim 1, wherein the relative movement is rotational movement substantially about a pivot axis extending through the body portion.

9. The biological sample collection device of claim 1, wherein said urging is resisted by a stop at or adjacent the open position.

10. The biological sample collection device of claim 1, comprising a locking means for locking said sample collection portion in at least one of said open position and said transfer position.

11. The biological sample collection device of claim 1, wherein the biological sample collection medium comprises an absorbent material for absorbing a liquid biological sample.

12. The biological sample collection device of claim 1, wherein the biological sample storage medium is held in a storage medium holding portion.

13. The biological sample collection device of claim 12, wherein the biological sample storage medium is removable from said storage medium holding portion.

14. The biological sample collection device of claim 1, wherein the biological sample storage medium comprises a planar membrane for absorbing liquid biological samples.

15. The biological sample collection device of claim 14, wherein the biological sample storage medium is held on a card.

16. The biological sample collection device of claim 1, made from a plastics material.

* * * * *